Figure 15:
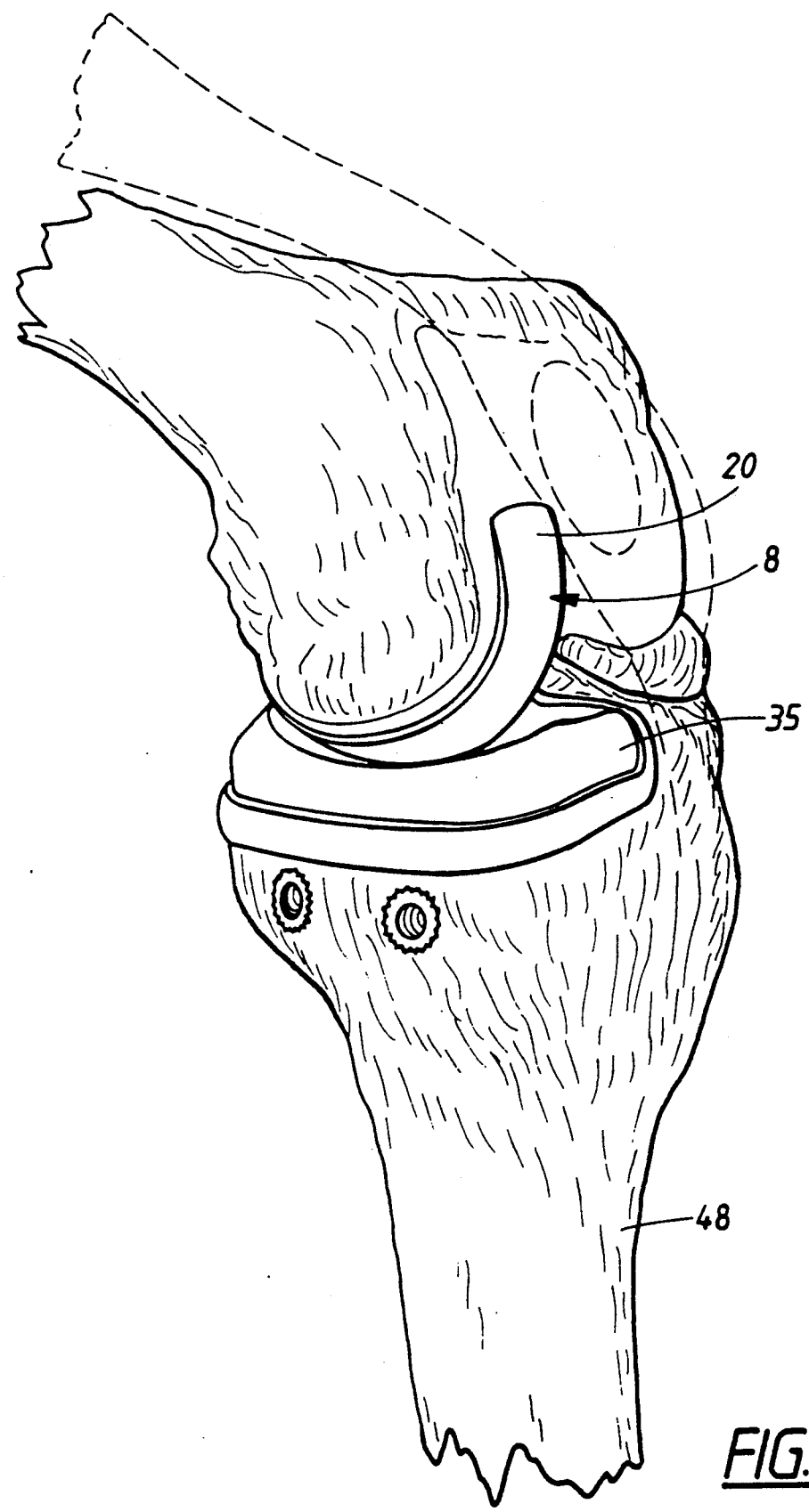

United States Patent [19]
Albrektsson et al.

[11] Patent Number: 5,037,439
[45] Date of Patent: Aug. 6, 1991

[54] KNEE-JOINT PROSTHESIS

[76] Inventors: Björn Albrektsson, c/o Wikander Värslevägen 39, Askim, Sweden, S-436 43; Stig Wennberg, Villa Holma Pl 16266, Angered, Sweden, S-424 57

[21] Appl. No.: 582,942
[22] PCT Filed: Apr. 11, 1989
[86] PCT No.: PCT/SE89/00193
 § 371 Date: Nov. 19, 1990
 § 102(e) Date: Nov. 19, 1990
[87] PCT Pub. No.: WO89/09578
 PCT Pub. Date: Oct. 19, 1989

[30] Foreign Application Priority Data
Apr. 11, 1988 [SE] Sweden .................................. 8801311

[51] Int. Cl.⁵ ............................. A61F 2/38; A61F 2/30
[52] U.S. Cl. .......................................... 623/20; 623/18
[58] Field of Search ............................. 623/16, 18, 20

[56] References Cited
U.S. PATENT DOCUMENTS

| 4,309,778 | 1/1982 | Buechel et al. | 623/20 |
| 4,673,407 | 6/1987 | Martin | 623/20 |
| 4,673,408 | 6/1987 | Grobbelaar | 623/20 |
| 4,838,891 | 6/1989 | Branemark et al. | 623/20 |

FOREIGN PATENT DOCUMENTS 0183669  6/1986  European Pat. Off. .............. 623/20

Primary Examiner—Ronald Frinks
Attorney, Agent, or Firm—Lerner, David, Littenberg, Krumholz & Mentlik

[57] ABSTRACT

Knee-joint prosthesis for permanent anchoring in the bone tissue of a knee-joint in the human body, consisting of a femur part, which comprises an articulation element (8) with a convex joint surface (20), an elongate intermediate element (7) with a first side, intended to bear against a surface of the bone tissue, and a second, opposite side intended to bear against an inner surface of the articulation element, which is arranged securely on the intermediate element by means of a positive locking. An anchoring element intended to be introduced into a recessed channel in the bone tissue and to be connected to this for anchoring the intermediate element and, thus, also the articulation element in the femur. The positive locking for securing the articulation element (8) for the femur on the intermediate element (7) in the femur part (3) is formed by means of the intermediate element being designed as a fixation rail with flanges (13) arranged on the second side of the intermediate element and by means of the rear surface of the articulation element for the femur being provided with an elongate fixation member (26) extending along this surface. This member is designed to be introduced into the said fixation rail and locked in the latter in a predetermined locking position by means of locking members (29).

3 Claims, 3 Drawing Sheets

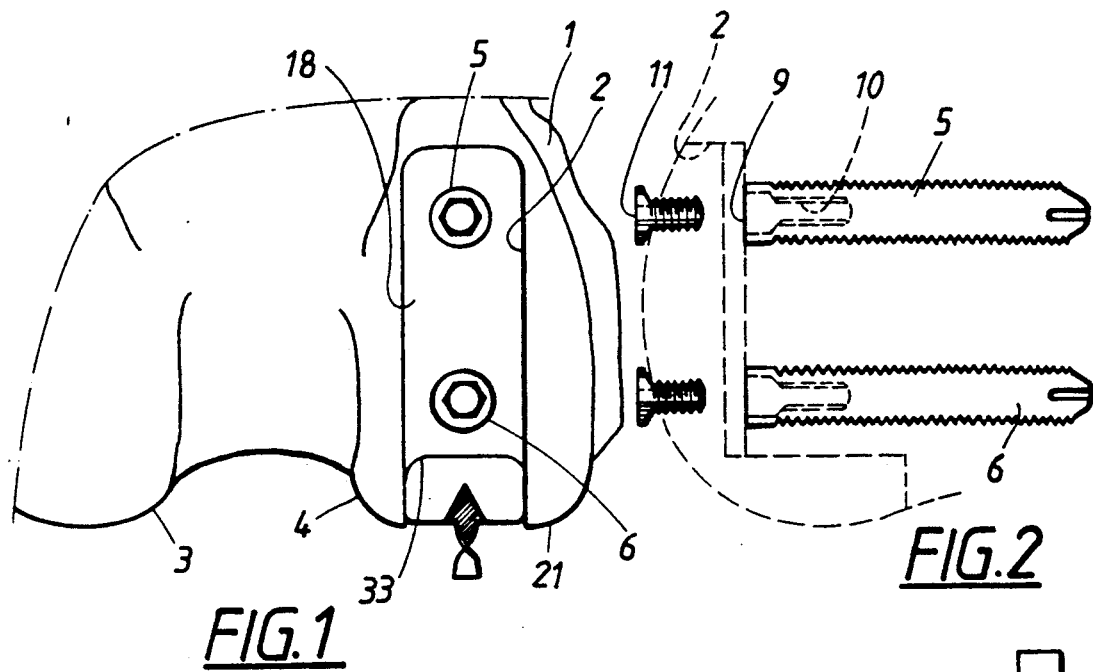
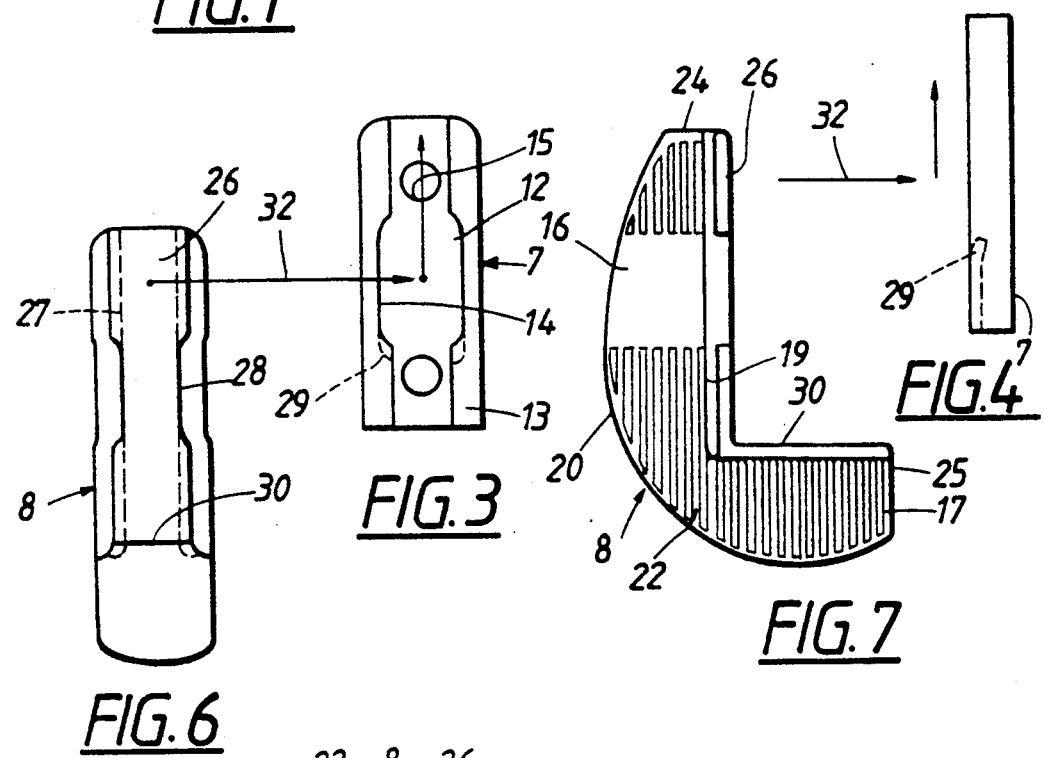
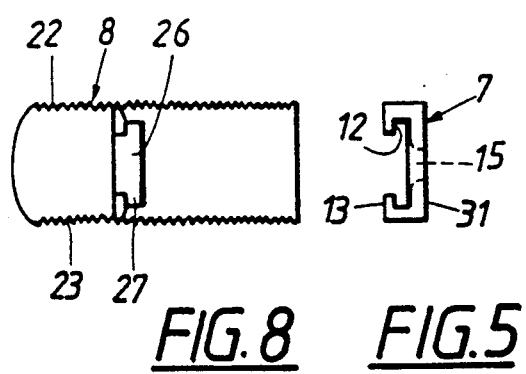

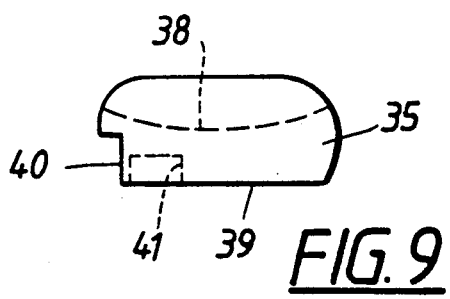
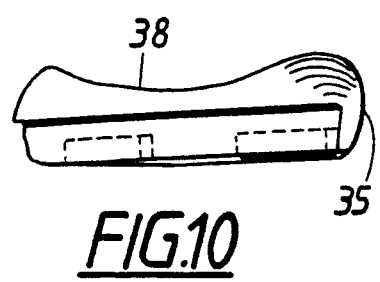
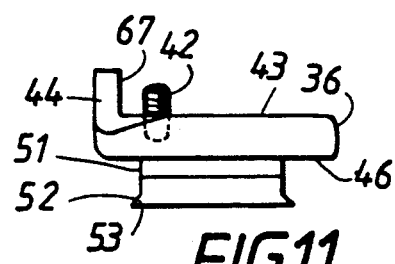
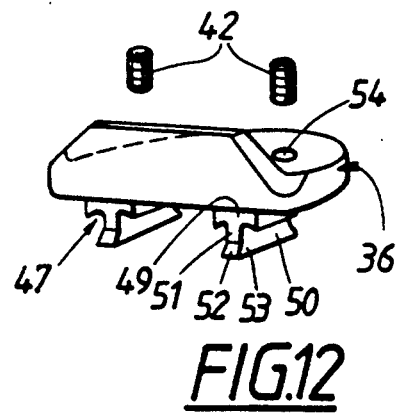
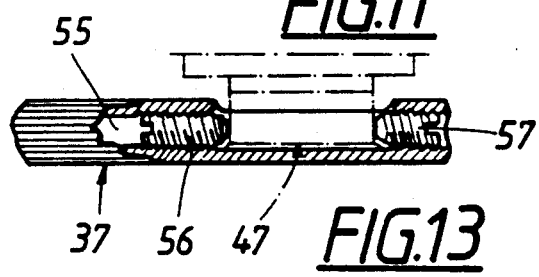
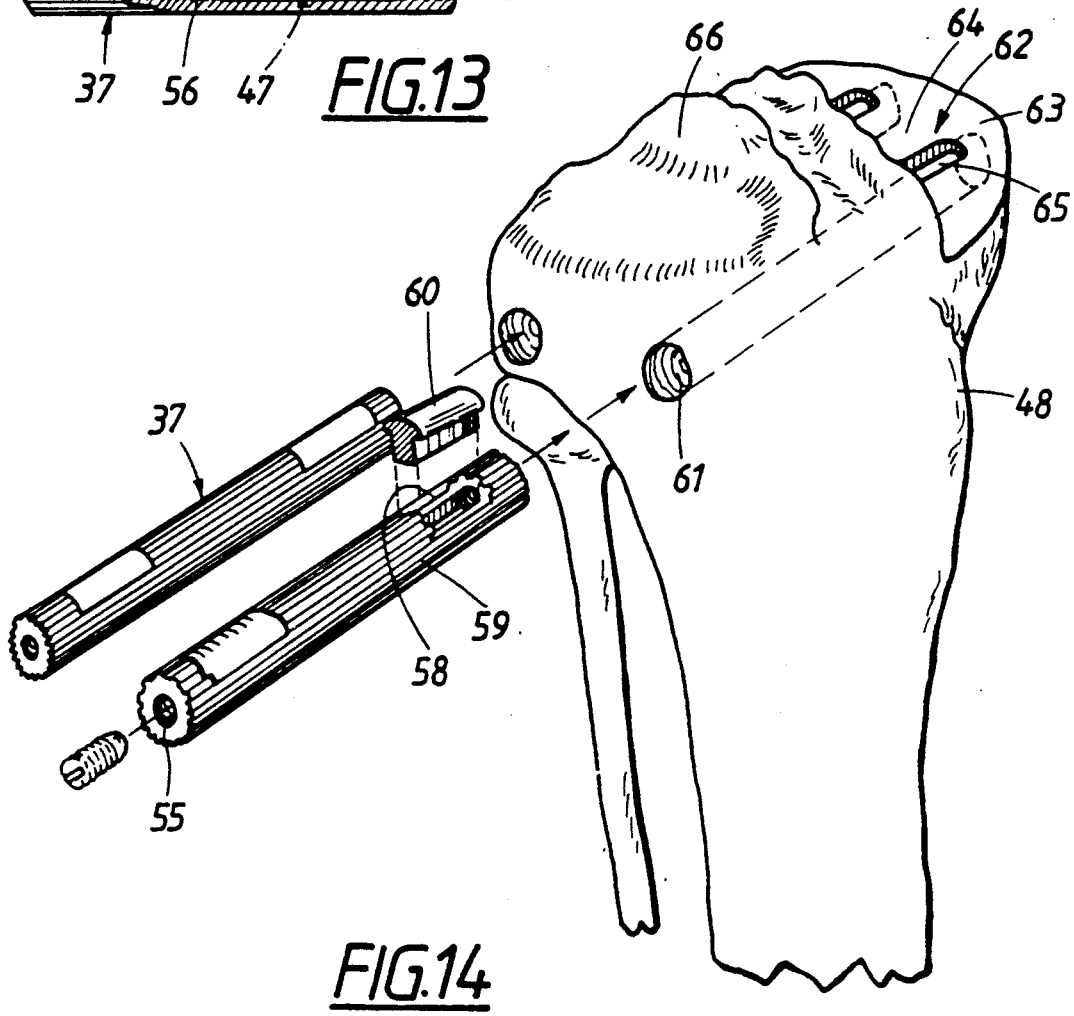

KNEE-JOINT PROSTHESIS

TECHNICAL FIELD

The present invention relates to a knee-joint prosthesis for unicompartmental joint surface replacement by permanent anchoring of the prosthesis in the bone tissue of a knee-joint in the human body, on the one hand consisting of a femur part, which comprises an articulation element with a convex joint surface, an elongate intermediate element with a first side, intended to bear against a surface of the bone tissue, and a second, opposite side intended to bear against an inner surface of the articulation element, in which respect the intermediate element is designed to be anchored in the bone tissue by means of at least one anchoring element intended to be introduced into a recessed channel in the bone tissue and to be connected to this, and in which respect the articulation element for the femur is designed to be locked on the intermediate element by means of a positive lock, and, on the other hand, a tibia part with a concave joint surface for cooperation with the convex joint surface of the femur part, and at least one anchoring element intended to be introduced into a recessed channel in the bone tissue for anchoring the tibia part in the tibia.

On the market and in clinical use there are at present a large number of knee-joint prostheses intended for permanent anchoring in the bone tissue. These prostheses are intended as replacement material in cases of morbid defects which have developed as a result of joint-destructive disorders, either degenerative disorders or rheumatism. The joint replacement material, which can replace parts of or all of the knee-joint, generally consists of a metal and polyethylene component, but there are also other material combinations such as, for example, a ceramic articulating with polyethylene. The metal component in artificial joints consists almost exclusively of one of three alloy types, so-called super alloys. These three alloys are stainless steel, which is now generally nitrogen-based with a high chromium content, cobalt chromium alloys or the titanium alloy Ti 6Al 4V. All these alloys contain metals which are potentially toxic. For example, aluminium has been shown to be neurotoxic. Chromium, which is included in steel and cobalt-based alloys, is considered to be carcinogenic. Nickel, which is also included in the same two alloys, is a powerful allergen In spite of the potential risks and despite the fact that certain of these alloys have been used for as long a period as 30 years or more, there have been surprisingly few reports which have given convincing evidence of material complications. However, in this context it should be added that it is only in the last 20 years that joint replacements of the said material have been available on a large scale.

In general it may be said that the knee-joint replacements available on the market today give reasonable results over a ten-year period, but the experiences with this type of material are largely limited to older patients with relatively low levels of activity. Complications have been reported to a fairly large extent. It is scarcely by chance that there is an abundance of different knee-prosthesis designs of different materials and with different biomechanical solutions. As regards previously known knee-joint replacements, none can be said to represent a definitive solution with respect to anchoring in the bone tissue, wear-resistance, joint stabilization or material strength. The central problem would appear to be the anchoring stability of the prosthesis components.

It is nowadays agreed that an as exact as possible contact fitting should be created between prosthesis component and bone tissue, regardless of whether the contact is established via a filling material or not. Filling material in the form of polymethyl methacrylate (PMMA) permits a more or less exact initial contact fitting between foreign material and bone tissue in the wider sense. Bone cement (PMMA) in the low-viscous form can, under pressure, be made to penetrate into the bone tissue and create a positive lock on the microplane. Since PMMA has a good adhesion to the prosthesis components, in this way a very good initial fixation is obtained. However, the disadvantage with PMMA is that chemical and thermal action on the bone tissue causes tissue damage and bone loss, in which respect the exact contact fitting initially obtained is completely or partially lost. Moreover, the bone cement has stability properties which, in the long term, lead to obvious risks of brittleness fractures with, as a consequence, inadequate contact surface with the bone tissue.

On account of observed and suspected complications secondary to the use of bone cement as filling material, for a good ten years laboratory work has been carried out on a number of prosthesis types which are anchored cement-free. The idea was to create a positive lock by using a more or less exact operative technique to adapt the contours of the bone ends, so that a good fit is obtained between the prosthesis components and the bone end. The positive lock which has been sought between non-cemented prosthesis and bone has been present on the microplane and macroplane in different prosthesis designs. An example of a positive lock on the macroplane is the ICLH prosthesis and its successors, where an operative technique rather than the prosthesis design itself afforded the conditions for a positive lock. The operative technique offered possibilities of guiding the cutting instruments in such a way that, on the one hand, it was possible to position the prosthesis exactly in relation to the mechanical axis of the knee-joint and, on the other hand, a bone-end contour was obtained which matched the smooth inner contour of the prosthesis. In a number of other prosthesis systems this principle has been used for macro-locking, but, in addition, a positive locking on the microplane has been sought by means of that surface of the prosthesis facing the bone tissue having a porous structure with opportunities for tissue to grow in. The in-growing tissue which appears is considered by prosthesis designers and manufacturers to be different from bone tissue, by reason of which a three-dimensional positive lock is obtained on the microplane with ideal stabilization, including osseointegration. However, this hope has not been fulfilled, judging from the histological findings of various retrieval studies. The in-growing of bone has, thus, only been observed in a limited sense. It has been found that femur prosthesis often have bone growing into the pore system, while the tibia prosthesis, which is the prosthesis component most prone to loosening, relatively rarely has such bone ingrowth. Furthermore, the bone ingrowth which does take place does not create direct contact with the bone tissue other than at points, and is separated from the tissue by a thin layer of fibrous tissue.

The fact that both cemented knee prosthesis and prosthesis intended for cement-free anchoring do not establish direct contact with the bone bed has been very clearly demonstrated by Ryd and co-workers from Lund. Using a stereoscopic x-ray method it was possible to show that both cemented and non-cemented prosthesis migrate, i.e. "slacken", especially during the first year after the implantation. It was also possible to demonstrate an instability of the prosthesis component. Thus, dynamically loaded knee-joint prosthesis move in relation to the bed of the bone. The clinical implications of Ryd's work are uncertain at present, but it is clear that both cemented and non-cemented prosthesis anchor in connective tissue, i.e. have a layer of connective tissue between the prosthesis component and bone seat.

The aim of the invention for which a patent is applied for is to improve the anchoring situation of knee-joint prostheses by providing for an exact match between prosthesis and bone tissue, i.e. a direct contact between metal and bone without any intermediate layer of connective tissue. This type of anchoring, which is called osseointegration, has been shown to be practicable in denture reconstruction using threaded titanium implants and is described by Albrektsson, T., Brånemark, P.-I., Hansson, H-A. and Lindström, J. 1981, "Osseointegrated titanium implants. Requirements for ensuring a longlasting, direct bone anchorage in man," Acta Orthop Scand 52, 155-170. Brånemark and co-workers have thus been able to show that, by adhering to certain basic principles, it is possible to achieve osseointegration and also to maintain this anchorage for a long period of time in the human jaw. In this connection clinical experience goes back over 20 years. The corner-stones which were considered by Brånemark and co-workers to be the conditions for achieving and maintaining osseointegration in cases of skeletal implantation are the use of prosthesis components made of commercially pure titanium, the screw design of the anchoring elements, and the fact that these and functional elements are introduced in two separate operations with an interval between them of about three months. The idea is that the incorporation of the implant is promoted by the fact that stress is not transmitted over the interface zone between bone and metal during the incorporation phase. An additional corner-stone in the reconstruction system is that the implant is introduced with the least possible tissue trauma, which presupposes a specially formulated operative technique in which the tissue is not subjected to supraliminal thermal and mechanical stimuli and where, moreover, the tissue is protected from tissue ischaemia by taking account of the vascular soft parts.

In an extremely wide-ranging experimental study Albrektsson and co-workers analysed the conditions for obtaining osseointegration in respect of the knee-joint. In this experimental work they assessed the effect of a number of different variables on incorporation parameters related to the achievement of osseointegration. They were able to establish that the use of commercially pure titanium probably creates better conditions for osseointegration than do alternative implant metals. They were also able to establish that the matching of the surgical defect to the implant is essential. The preconditions for osseointegration were also shown to be considerably more favourable if screw connections were used instead of alternative connections such as spikes or perforated plates. They also succeeded in showing, and this is an entirely new observation, that joint replacements made of pure titanium can be made to osseointegrate in a one-stage process. This is, of course, important information, since the two-stage process, which was considered by Brånemark and co-workers as a precondition for osseointegration, entails practical difficulties, especially in a joint application. It is thus only with great reluctance that surgery will be carried out on a knee-joint in two separate operations, bearing in mind the risk of interference with sliding surfaces and displacement layers in the soft parts. The risk of development of capsule fibrosis, with reduction in the volume of the joint cavity, increases with each intra-articular intervention.

Therefore, in summary, it may be said that the aim of the present invention was to develop an osseointegrated knee-joint prosthesis which satisfies some, but not all, of the requirements which have been regarded as being preconditions for osseointegration of jaw implants. It is desired to avoid a two-stage process in the installation of the artificial joint replacement material, at least at the femur end, where a two-stage process is difficult to carry out without the joint being opened twice, and where, moreover, experimental studies indicate that simultaneous installation of anchoring and functional elements is consistent with osseointegrated anchorage. To the extent that two separate operations have been thought necessary for achieving osseointegration at the tibia end, a technique has been sought for carrying out the first intervention extra-articularly, i.e. without going into the knee-joint. The objective has been that the surgical work required to instal the knee-joint prosthesis, in respect of which a patent is applied for, on the one hand should comprise a first operation in which anchoring screws are introduced extra-articularly into the tibia end and, on the other hand, a second operation about three months later, when both anchoring element and joint element are installed in the femur end and the joint element is connected to the anchoring element osseointegrated at the tibia end.

The principle in respect of which a patent is applied for differs from other non-cemented prosthesis designs for the knee-joint. The principle is based partly on previously known principles, see for example SE 450,336 or EP 0,183,669, but, as emerges from the text below, we have not only improved but also radically altered the known design solution which has several important disadvantages. The most important objection is that no information has been given regarding methods for cutting bone tissue in a way which permits an exact initial contact fitting by atraumatic techniques; nor has it been possible to offer any solution to the positioning problem which is fundamental to achieving a preserved, osseointegrated anchorage permitting biomechanics. Without suitable cutting techniques and positioning techniques, it may be said that the design previously patented, or for which a patent is applied for, is no more than a drawing-board product. Moreover, in the cited design solutions, insufficient consideration has been given to wearing problems connected with the use of commercially pure titanium in sliding surfaces against polyethylene. It is true that it has been considered possible to compensate for the wear resistance of pure titanium by means of surface modification of the titanium joint surface. In extensive laboratory tests carried out during 1987 it was found that surface modification of pure titanium, which was previously considered possible for achieving acceptable wear resistance, does not provide such resistance. Instead, all experimental experience indicates that part of the artificial joint which bears against plastic or other material cannot consist of commercially pure titanium, which is altogether too soft, regardless of whether or not its surface has been hardened. The tests carried out show that one precondition for achieving sufficient wear resistance is that the articular head of the prosthesis be made of surface-modified titanium alloy. In theory, from the point of view of wear, it should also be possible for the articular head to be made of cobalt-based alloy, but then there is also an obvious risk of galvanic corrosion.

Moreover, it may be added that these previously known knee-prosthesis designs involve, in addition to the abovementioned disadvantages, a number of inadequately thought-out solutions, particularly as regards mechanical connections entailing risks of insufficient prosthesis function, regardless of whether the implant has or has not been osseointegrated. As far as the patented design solution is concerned, it is also doubtful whether conditions for osseointegration exist at all, bearing in mind that the anchoring elements are not made up of screws of the type with which one has experience in jaw reconstruction material, but rather of grooved plugs in the form of a double barrel where the plugs are joined with a plate. This type of implant design has been shown by Carlsson and co-workers (1986) to give poor conditions for osseointegration, and it may thus be said that the whole design solution which is offered in this known design solution can be called into question. It is at least clear that, regardless of whether a two-stage process is used or not, there is no experimental basis for assuming that osseointegration can be achieved with this design other than in exceptional cases.

As regards the prosthesis design according to EP 0,183,669 it may be stated that this too has a number of disadvantages, even if not quite as obvious as in the version according to SE 450,336. The prosthesis design, as described in SE 450,336, comprises several inadequate mechanical connections. Moreover, the recommended reconstruction procedure creates an unfavourable biomechanical situation with a necessary moment arm which threatens to thwart the osseointegration which was probably obtained initially. In the version according to EP 0,183,669 an attempt has been made to compensate for this by building in a superficial, crosswise, flat connection arm between the two grooved anchoring elements in each tibia condyle. This certainly relieves some of the stress which was obtained by the moment arm which is formed between the anchoring element and the periphery of the plateau of the tibia. If there is an excess load medially along the tibia prosthesis, then the transverse arm reduces the torsional moment against the medial anchoring element, but especially at the front end where the arm is positioned, and at the same time a cranially-directed force vector is obtained on the contralateral anchoring element, which risks dislodging the osseointegration on the side. Thus, the stress distribution in the proximal tibia is by no means uniform, nor can one reliably avoid excess loads which have disastrous consequences for the osseointegration connection. In addition, both the connection arm and the anterior-posterior direction of the anchoring elements mean that it is not possible to prevent outwardly projecting implant material from lying in close contact with the skin, with the risk of perforation upon direct force, and then also the risk of contamination and secondary infection.

As regards the mechanical connections between anchoring element and joint element, as described in EP 0,183,669, it may be said that there are several unreliable points, in particular concerning the connection between the articulation part of the femur prosthesis and the intermediate element which, on the one hand, causes production-technology difficulties with guide spikes and spring-action pins and, on the other hand, provides insufficient positive locking, with a risk of the prosthesis tipping in the lateral direction unless it is certain that the bone walls in the bone bed of the articulation element afford sufficient positive locking.

The intermediate element, which is L-shaped in the previous version and therefore involves difficulties both in production technology and in surgical techniques, has therefore no force-transmission lock of the type which is included in the prosthesis design solution according to the present invention. In the previous version a spring-action pin was relied upon to sufficiently compensate for shear stresses in the anterior-posterior direction. It is doubtful whether a spring pin can offer the anchoring stability which is required between articulation element and intermediate element, and it is also doubtful whether the spring principle functions at all. If, in conjunction with the pressing-on of the articulation element, tissue fragments enter the hole for the spring pin, there is a risk that the pin will not go into its hole at all, or will only go into this partially, with inadequate anchoring stability as a result. Another disadvantage of a spring-action pin of the type mentioned in EP 0,183,669 is the difficulty involved in removing the articulation element in the femur once it has been positioned in a highly stable manner. A precondition for removing the element is, therefore, that a hole be bored through the prosthesis joint surface.

Another important disadvantage of the femur prosthesis in the previously known prosthesis version is the difficulty involved in matching the bone bed to the covering part of the contact surface of the articulation element against the polyethylene component. In cross-section the articulation element has a mushroom shape, and it is assumed that it will be possible to adapt the underside of the mushroom cap to the bone seat, but how such a contact is to be achieved is not stated, and there are obvious difficulties in solving this cutting problem in surgical practice.

The aim of the present invention is to provide a knee-joint prosthesis which gives a stable and resistant anchoring in both the femur and tibia by means of positive locking and by establishing direct contact between prosthesis and bone tissue.

SOLUTION

The said aim is achieved by means of the knee-joint prosthesis according to the present invention, which is characterized in that the positive locking for securing the articulation element for the femur on the intermediate element in the femur part is formed, on the one hand, by the intermediate element being designed as a fixation rail with flanges arranged on the said second side of the intermediate element and, on the other hand, by the rear surface of the articulation element for the femur being provided with an elongate fixation member extending along the said surface and designed to be introduced into the said fixation rail and locked in the latter in a predetermined locking position by means of locking members, and in that the positive locking consists of an open channel arranged in the intermediate element and with two flanges directed towards each other and formed with at least one recess arranged in each flange, and in that the said fixation member consists of a fixation element with an essentially T-shaped cross-section and with a number of flanges divided up by recesses so that the articulation element can be fixed on the intermediate element by means of at least one of the flanges of the fixation member being introduced via the said recesses in the intermediate element into the channel transverse to its longitudinal direction and moved along the channel inside its flanges to the said locking position, which is determined by the said locking members which consist of locking shoulders, formed in the flanges of the intermediate element and designed to project into the channel.

The invention will be described in greater detail below on the basis of an exemplary embodiment and with reference to the attached drawings, in which FIGS. 1 and 2 show anchoring elements incorporated in a femur part of a knee-joint prosthesis according to the invention and mounted in the femur of a human body, FIGS. 3, 4 and 5 show different views of a fixation rail incorporated in the femur part of the knee-joint prosthesis, while FIGS. 6, 7 and 8 show different views of an articulation element incorporated in the femur part of the knee-joint prosthesis. FIGS. 9 and 10 show two different views of a movable tibia plateau incorporated in the tibia part of the knee-joint prosthesis, FIGS. 11 and 12 show two views of a fixed tibia plateau incorporated in the tibia part of the knee-joint prosthesis, FIG. 13 shows a longitudinal section through an anchoring element incorporated in the tibia part, while FIG. 14 shows a perspective view of the upper part of the tibia and an exploded view of the contemplated position of the anchoring elements, and FIG. 15 shows a perspective view of a knee-joint in which the knee-joint prosthesis is mounted.

As can be seen in FIGS. 1 and 2 the femur part 1 of an individual's knee-joint has been provided, by cutting using a surgical instrument, with an essentially L-shaped recess 2, intended to accommodate with great precision the femur part of a knee-joint prosthesis. The femur part of an individual's knee-joint consists of two joint surfaces 3, 4. In certain cases both joint surfaces need to be replaced with a femur part of the knee-joint prosthesis, but in the majority of cases only the one joint surface has to be replaced. For the sake of simplicity the following description deals only with one femur part of a knee-joint prosthesis. The femur part of the knee-joint prosthesis according to the invention consists of three main parts, namely anchoring elements 5, 6, fixation rail 7 and articulation element 8.

As is shown best in FIG. 2, in the example shown the anchoring elements 5, 6 are two in number and are designed as grooved spikes with, for example, annular grooving extending peripherally. The anchoring elements, which are essentially cylinder-shaped, are introduced into cylindrical channels which have been made in advance by drilling and are directed straight from the front into the bone tissue of the femur part of the knee-joint. The anchoring elements are positioned at a carefully defined mutual distance and position relative to the recess 2 made in the bone tissue. The outer ends 9 of the anchoring elements 5, 6 are moreover provided with threaded recesses 10 each intended to receive a fixation screw 11 in the shape of, for example, a hexagonal screw.

The fixation rail 7 has a C-shaped cross-sectional form and in this way encloses a channel 12 with two flanges 13 directed towards each other, see FIG. 5. The flanges 13 have two recesses 14 situated centrally in front of each other, see FIG. 3. The fixation rail 7 also has two circular openings 15 with countersinks for receiving the heads of the fixation screws 11. It is important that the heads of the fixation screws should not protrude above the bottom of the channel.

The articulation element 8 consists of an angular element which is essentially L-shaped with two sections 16, 17 extending at right angles relative to each other and with boundary surfaces intended to be in contact with surfaces in the recess 2 in the bone tissue, with the fixation rail lying between the bottom 18 of the recess and the inside 19 of the section 16. On the outside the two sections 16 and 17 have a common convex-curved joint surface 20 of a shape designed to follow the joint surface 21 of the knee-joint, and in so doing compensating for worn-down sections. The remaining boundary surfaces of the articulation element 8 consist of two essentially plane, parallel side surfaces 22, which are advantageously grooved or provided with another coarse surface structure in order to thereby facilitate anchoring in the bone tissue in the form of osseointegration. The two sections 16, 17 also have plane end surfaces 24, 25, which are expediently at right angles to the inner sides of the sections.

As emerges from FIGS. 7 and 8, the vertical inner side 19 of the articulation element 8 has a fixation element 26 which extends over this inner side and has an essentially T-shaped cross-section with two laterally directed longitudinal flanges 27. This fixation element 26 is dimensioned so as to fit into the channel 12 of the fixation rail 7. As emerges best from FIG. 6, the fixation element 26 has two recesses 28 which are situated in front of each other and are dimensioned so as to accommodate the lower sections, situated in front of each other, of the flanges 13 of the fixation rail, in which connection the two flanges 27 of the fixation element 26 can be introduced, by their upper sections situated in front of each other, into the two recesses 14 of the fixation rail upon mounting of the prosthesis, as will be described in greater detail below. The flanges 13 in the fixation rail 7 are, moreover, bent slightly inwards at least one end or two ends of the recesses 14 in order to form locking members in the form of locking shoulders 29, by means of which the fixation element of the articulation element can be locked in the fixation rail. The horizontal inner side 30 of the articulation element does not have any laterally directed flanges, but only a bevelling and otherwise a plane surface.

The fixation rail 7 is thus anchored by means of the anchoring elements 5, 6 with its channel 12 directed outwards and with its plane inner side 31 bearing against the bottom of the recess 18 in the bone tissue. The fixation rail is held securely on the anchoring elements by means of the fixation screws being introduced through the holes 15 in the fixation rail and screwed into the anchoring element. The articulation element 8 is fitted by means of its fixation element 26 being brought towards the fixation rail in the direction of the arrow 32 so that the upper section of the flanges 27 can be introduced into the recesses 14 of the fixation rail to bear against the bottom of the rail so that the flanges 26, 27 of the fixation element can be brought inside the flanges 13 in the fixation rail by means of the articulation element being moved slightly upwards until the inner side 30 of the section 17 bears against the surface 33 of the recess 2 in the bone tissue. In this way the locking shoulders 29 bear resiliently against the bottom of the channel 12 and are inclined so that they form a positive locking for the articulation element together with the fixation element 26 in the fixation rail. The positive locking is thus designed to allow the articulation element 8 to be introduced into the fixation rail 7 but to block against displacement movement in the opposite direction in the fixation rail. This anchoring of the articulation element 8 provides a particularly good anchorage and permits force transmission in different directions, without relying on the side walls of the bone bed.

The tibia part of the knee-joint prosthesis is likewise made up of three main elements, namely a movable tibia plateau 35, a fixed tibia plateau 36 and anchoring elements 37. The movable tibia plateau, which replaces the meniscus, has a concave joint surface 38 intended to cooperate with the joint surface 20 of the articulation element 8 in the femur part. Furthermore, the movable tibia plateau has a flat sliding surface 39, which is situated opposite the concave joint surface, and a recess 40 extending along one side of the movable tibia plateau. Moreover, two recesses 41 are arranged in the sliding surface 39 for guide pins 42 which are anchored in the fixed tibia plateau 36. The recesses 41 are made with a greater size than the pins 42 in order to permit mobility of the movable tibia plateau 35 relative to the fixed tibia plateau 36 by means of sliding contact between the sliding surface 39 and a corresponding flat, upwardly directed sliding surface 43 of the fixed tibia plateau 36.

The fixed tibia plateau 36 is designed as an essentially plate-shaped element with the said flat sliding surface 43 and an upwardly directed support flange 44 designed to be accommodated in the recess 40 in the movable tibia plateau for lateral control of the latter. The support flange 44 has bevels 45 on both sides in order to eliminate outwardly projecting corners. The plate-shaped element has, on its underside, an essentially flat bearing surface 46 which extends parallel to the sliding surface 43 and has two locking bases 47 which are arranged with a space between them and are mutually parallel, these being intended to cooperate with the anchoring elements 37 for anchoring the fixed tibia plateau 36 on the tibia 48 (shin bone). The locking bases 47 extend at essentially right angles to the longitudinal direction of the flange 44 and are designed as two elongate flanges or strips with an essentially T-shaped cross-section and a base part which has two laterally directed longitudinal flange sections 49 and one vertical flange section 50. At its ends the flange section 50 has flat end surfaces 51, which are essentially at right angles to the fixation surface 46, but merge into inclined bevels 52 which form two opposite projections 53. The guide pin 42 is expediently anchored securely in the fixed tibia plateau 36, for example by fixing in bores 54 in the sliding surface 43.

In the example shown the anchoring elements 37 are two in number and consist of essentially cylindrical rod elements with longitudinal grooves and a continuous, axially extending threaded channel 55, in which two adjusting and locking screws 57 inserted from opposite directions are threaded. The anchoring elements 37 also have at least one recess 58 in their grooved circumferential surface 59. The recess 58 is of such a shape and such a length that the locking bases 47 can be introduced into the recesses and their flanges 50 can extend inside the channel 55, as shown in FIG. 13 with dot-and-dash lines. The anchoring elements 37 also have a protection plug 60 for each recess 58, which plug keeps the channel and the recess 58 free from tissue material and the like during insertion of the anchoring elements into the tibia 48.

As emerges from FIG. 14, the anchoring elements 37 are intended to extend mutually parallel and laterally into the tibia, each one into its respective laterally directed channel 61, which has been recessed in the proximal part of the tibia.

In addition to these two cylindrical recesses 61, also arranged in the tibia 48 is a step-like recess 62 with two essentially plane boundary surfaces 63, 64 which are expediently at right angles to each other. The cylindrical channels 61 extend through the tibia below the one boundary surface 63 of the recess 62 at a distance which corresponds essentially to the height of the laterally directed flange sections 49 of the locking bases 47. In the mounted state in the tibia, right in front of the recesses 58 in the anchoring elements 37 there are arranged openings 65 in the boundary surface 63 of the tibia 48 with an extension which essentially corresponds to the extension of the recesses 58.

The tibia part of the joint prosthesis is held together in the following way. With the anchoring elements 37 introduced into their respective channel-shaped recesses 61 in the tibia, and with the protection plugs 60 removed via the openings 65, the fixed tibia plateau 36 is secured by means of the locking bases 47 projecting in through the openings 65 and the recesses 58 in the anchoring elements 37. This position emerges most clearly from FIG. 13, which shows a section of the fixed tibia plateau with dot-and-dash lines. The locking bases 47 project into the channels 55 of the anchoring elements, in which respect the adjusting and locking screws 56, 57 in an initial position are located at a back position in which they do not project into the recesses 58. With the locking bases 47 introduced into the recesses 58, they are locked in the anchoring elements 37 by screwing the adjusting and locking screws forward so that their front and slightly conical ends bear against the end surfaces 51 of the locking bases, in which respect locking is effected by means of the projections 52 pushing in below the conical ends of the screws 56, 57. The threaded channel 55 is advantageously slightly widened in front of the recesses 58 and has no threading there. The length of the recesses 58 in the axial direction of the anchoring elements is adapted in relation to the length of the locking bases in such a way that there is an adjusting space in the recesses, by means of which the fixed tibia plateau 36 can be finely adjusted as regards its distance from the boundary surface 64 of the recess 62 in the tibia. By means of this adjustment possibility, it is therefore possible, by means of the screws 56, 57 in the anchoring elements 37, for the fixed tibia plateau to bear satisfactorily against this boundary surface 64 and also against the boundary surface 63 by means of the fixed tibia plateau 36 being pressed against the surface 63 during tightening of the screws 56, 57. With good matching of the position of the channels 61 relative to the surface 63, the bevelled surfaces 52, in cooperation with the conical ends of the screws 56, 57 in the locking moment, permit tightening and pre-stressing of the lower fixation surface 46 of the fixed tibia plateau against the recessed boundary surface in the tibia by virtue of the fact that the fixed tibia plateau tends, because of the tightening of the screws, to move towards the anchoring elements.

For the tibia part too of the knee-joint prosthesis, the replacement of only the one joint surface has been described above, while, as emerges from FIG. 14, the remaining joint surface 66 is unaffected. Replacement of the second joint surface 66 too thus requires an additional recess 62 with openings 65 to the channels 61 for the anchoring element 37, which is thus used jointly in the double knee-joint prosthesis. For this purpose, two symmetrically positioned recesses 58 are arranged in each anchoring element 37.

FIG. 15 shows a knee-joint whose one side is replaced by a knee-joint prosthesis according to the present invention, in which respect it emerges how the femur part of the knee-joint prosthesis is positioned relative to the tibia part. The convex joint surface 20 of the articulation element 8 of the femur part, which joint surface 20 forms the load-absorbing part of the knee-joint ball, bears on the concave joint surface 38 of the movable tibia plateau. There are thus no mechanical connections between the femur part and the tibia part of the knee-joint prosthesis, but rather they are held together by means of the natural ligaments of the knee-joint, which thus permits a to a large extent free and natural movement of the knee-joint with the knee-joint prosthesis. The movable tibia plateau is allowed to move during the joint movement on account of the sliding contact between the flat bearing surfaces 39, 43 and also the transverse bearing surfaces 40, 67, this being permitted by the movement of the guide pins 42 in the enlarged recesses 41. A certain movement is permitted in all directions parallel to the plane of the bearing surfaces 39, 43. It is thus also possible for the bearing surfaces 40, 67 in certain positions to have a mutual intermediate space.

The fact that the anchoring elements 37 are directed laterally makes it possible for them to be fitted without the knee-joint at the same time being opened, which is important from the point of view of the patient. This therefore avoids penetrating into the tibia from the front where the bone has the shape of a snow-plough, with the associated risks of projecting implant parts with sharp edges coming into conflict with the skin. The fact that the anchoring elements are introduced into the side of the tibia also provides a larger contact surface between anchoring element and bone tissue, due to the oval shape of the tibia cross-section. In addition, the moment arms, which are the consequence of introducing the anchoring elements from the front, are avoided. Furthermore, an extremely reliable mechanical connection is achieved between the anchoring element and the fixed tibia plateau, which gives a secure positioning of the fixed tibia plateau in the tibia.

The invention is not limited to the embodiment described above and shown in the drawings, but can be varied within the scope of the subsequent patent claims. For example, it is conceivable for the fixation rail 7 in the femur part of the prosthesis element and the fixation part 26 in the articulation element 8 to have the reverse appearance, so that the fixation element instead has a T-shaped cross-section, while the fixation part 26 has a C-shaped cross-section. It is also conceivable for the recesses 14, 28 to be omitted, even although this makes introduction of the articulation element more difficult, since this must then be effected from the end of the fixation rail. In this connection the locking members must be designed in another way. Moreover, it is conceivable for the tibia part of the knee-joint prosthesis to have a construction other than that which has been shown and described. Thus, it is in principle conceivable for the articulation element for the tibia not to be divided up into a fixed and a movable part. The circumferential surface of the anchoring elements can have another structure, for example helicoidal grooves, so that the anchoring elements can be screwed into the bone tissue.

We claim:

1. Knee-joint prosthesis for unicompartmental joint surface replacement by permanent anchoring of the prosthesis in the bone tissue of a knee-joint in the human body, on the one hand consisting of a femur part, which comprises an articulation element (8) with a convex joint surface (20), an elongate intermediate element (7) with a first side, intended to bear against a surface of the bone tissue, and a second, opposite side intended to bear against an inner surface of the articulation element, in which respect the intermediate element is designed to be anchored in the bone tissue by means of at least one anchoring element (5, 6) intended to be introduced into a recessed channel in the bone tissue and to be connected to this, and in which respect the articulation element for the femur (1) is designed to be locked on the intermediate element by means of a positive lock, and, on the other hand, a tibia part with a concave joint surface (38) for cooperation with the convex joint surface of the femur part, and at least one anchoring element (37) intended to be introduced into a recessed channel (61) in the bone tissue for anchoring the tibia part in the tibia (48), characterized in that the positive locking for securing the articulation element (8) for the femur on the intermediate element (7) in the femur part (3) is formed, on the one hand, by the intermediate element being designed as a fixation rail with flanges (13) arranged on the said second side of the intermediate element and, on the other hand, by the rear surface of the articulation element for the femur being provided with an elongate fixation member (26) extending along the said rear surface and designed to be introduced into the said fixation rail and locked in the latter in a predetermined locking position by means of locking members (29), and in that the positive locking consists of an open channel (12) arranged in the intermediate element (7) and with two flanges (13) directed towards each other and formed with at least one recess (14) arranged in each flange, and in that the said fixation member (26) consists of a fixation element (26) with an essentially T-shaped cross-section and with a number of flanges (27) divided up by recesses (28) so that the articulation element (8) can be fixed on the intermediate element by means of at least one of the flanges of the fixation member (26) being introduced via the said recesses in the intermediate element into the channel transverse to its longitudinal direction and moved along the channel inside its flanges (13) to the said locking position, which is determined by the said locking members (29) which consist of locking shoulders, formed in the flanges of the intermediate element and designed to project into the channel.

2. Knee-joint prosthesis according to claim 1, characterized in that the said recesses (14) in the intermediate element (7) consist of one recess for each flange (13), which two recesses are located in front of each other, dividing each of the said flanges into essentially two flange sections of identical size.

3. Knee-joint prosthesis according to claim 2, characterized in that the said recesses (14) in the intermediate element have a length which essentially corresponds to the length of the said flange sections.

* * * * *